(12) United States Patent
Cottrell et al.

(10) Patent No.: US 7,396,820 B2
(45) Date of Patent: *Jul. 8, 2008

(54) ANTHELMINTIC FORMULATIONS

(75) Inventors: Ian Cottrell, Basking Ridge, NJ (US);
Arima Das Nandy, Congers, NY (US);
Albert Ahn, Short Hills, NJ (US);
Richard Fisher, Somerset, NJ (US)

(73) Assignees: Virbac Corporation, Fort Worth, TX (US); The Hartz Mountain Corporation, Secaucus, NJ (US)

( * ) Notice: Subject to any disclaimer, the term of this patent is extended or adjusted under 35 U.S.C. 154(b) by 204 days.

This patent is subject to a terminal disclaimer.

(21) Appl. No.: 10/800,407

(22) Filed: Mar. 12, 2004

(65) Prior Publication Data

US 2005/0032719 A1    Feb. 10, 2005

Related U.S. Application Data

(63) Continuation-in-part of application No. 10/637,807, filed on Aug. 8, 2003.

(51) Int. Cl.
*A61K 31/70* (2006.01)

(52) U.S. Cl. ..................................................... 514/30

(58) Field of Classification Search .................. 514/30
See application file for complete search history.

(56) References Cited

U.S. PATENT DOCUMENTS

| | | | |
|---|---|---|---|
| 3,502,661 A | 3/1970 | Kasubick et al. |
| 3,954,791 A | 5/1976 | Loewe et al. |
| 3,993,682 A | 11/1976 | Kolling et al. |
| 4,001,411 A | 1/1977 | Seubert et al. |
| 4,199,569 A | 4/1980 | Chabala et al. |
| 4,283,400 A | 8/1981 | Von Bittera et al. |
| 4,447,414 A | 5/1984 | Gay et al. |
| 4,597,969 A | 7/1986 | Maxfield |
| 4,666,939 A | 5/1987 | Voege et al. |
| 4,717,566 A | 1/1988 | Eckenhoff et al. |
| 4,814,347 A | 3/1989 | Nelson |
| 4,988,696 A | 1/1991 | Andrews et al. |
| 5,036,069 A | 7/1991 | Andrews et al. |
| 5,093,334 A | 3/1992 | Andrews et al. |
| 5,536,715 A | 7/1996 | Hood |
| 5,538,989 A | 7/1996 | Kyle |
| 5,550,153 A | 8/1996 | Kerz |
| 5,756,474 A | 5/1998 | Furstenau |
| 5,824,653 A | 10/1998 | Beuvry et al. |
| 5,840,324 A | 11/1998 | Hennessy et al. |
| 5,861,142 A | 1/1999 | Schick |
| 6,201,012 B1 * | 3/2001 | Lowndes et al. ............ 514/460 |
| 6,207,179 B1 | 3/2001 | Mihalik |
| 6,340,672 B1 | 1/2002 | Mihalik |
| 6,492,340 B2 | 12/2002 | Mihalik |
| 6,503,536 B2 | 1/2003 | Kalbe et al. |
| 6,521,610 B2 | 2/2003 | Tiebes et al. |
| 6,524,602 B1 | 2/2003 | Burkhart et al. |
| 6,541,455 B2 | 4/2003 | Pearlman |
| 6,552,002 B2 | 4/2003 | Steber et al. |
| 6,562,363 B1 | 5/2003 | Mantelle et al. |
| 6,596,714 B1 | 7/2003 | Mihalik |
| 6,596,727 B1 | 7/2003 | Schaper et al. |
| 6,605,595 B1 | 8/2003 | Omura et al. |
| 6,617,314 B2 | 9/2003 | Grosse-Bley et al. |
| 6,627,613 B2 | 9/2003 | Strobel |
| 6,663,879 B2 | 12/2003 | Harvey |
| 6,764,999 B2 | 7/2004 | Bachman et al. |
| 6,858,601 B2 | 2/2005 | Mihalik |
| 6,872,708 B2 | 3/2005 | Matsumoto et al. |
| 6,903,052 B2 | 6/2005 | Williams et al. |
| 2003/0055089 A1 | 3/2003 | Sirinyan et al. |
| 2003/0068365 A1 | 4/2003 | Suvanprakorn et al. |
| 2003/0077297 A1 | 4/2003 | Chen et al. |
| 2003/0119852 A1 | 6/2003 | Beckmann et al. |
| 2003/0144251 A1 | 7/2003 | Wu et al. |
| 2003/0203891 A1 | 10/2003 | Goebel et al. |
| 2003/0236203 A1 | 12/2003 | Freehauf et al. |
| 2004/0006047 A1 | 1/2004 | Schaper et al. |
| 2004/0018241 A1 | 1/2004 | Houze et al. |
| 2004/0019062 A1 | 1/2004 | Mihalik |
| 2004/0037869 A1 | 2/2004 | Cleverly et al. |
| 2004/0043925 A1 | 3/2004 | Kalbe et al. |
| 2004/0151722 A1 | 8/2004 | Bishop |
| 2004/0162283 A1 | 8/2004 | Geobel et al. |
| 2004/0180034 A1 | 9/2004 | Hughes et al. |
| 2004/0224012 A1 | 11/2004 | Suvanprakron et al. |
| 2004/0234579 A1 | 11/2004 | Finke |
| 2004/0234580 A1 | 11/2004 | Huber et al. |
| 2005/0032718 A1 | 2/2005 | Burke et al. |

(Continued)

FOREIGN PATENT DOCUMENTS

EP       0 059 074    10/1984

(Continued)

OTHER PUBLICATIONS

PCT International Search Report dated Dec. 14, 2004 for International Application No. PCT/US04/25006.

(Continued)

*Primary Examiner*—Elli Peselev
(74) *Attorney, Agent, or Firm*—Patterson & Sheridan, L.L.P.

(57) ABSTRACT

The present invention provides a method for preparing a pharmaceutical formulation containing ivermectin and a method and composition that can contain ivermectin plus hexahydropyrazinoisoquinolines, tetrahydropyrimidines and benzimidazoles or febantel. Examples of hexahydropyrazinoisoquinolines, tetrahydropyrimidines and benzimidazoles include praziquantel, pyrantel pamoate and fenbendazole, respectively. A pharmaceutical formulation is provided for use in the treatment of helminthiasis of mammals, and particularly tapeworm, hookworm, roundworm, whipworm and heartworm of domestic animals and farm animals. The present invention also provides a method of treating helminthiasis in mammals, which method comprises administering to the mammal in need thereof an anthelmintically effective amount of a pharmaceutical formulation of the invention.

25 Claims, No Drawings

U.S. PATENT DOCUMENTS

2005/0032719 A1    2/2005    Cottrell et al.
2005/0118241 A1    6/2005    Landschaft
2005/0136087 A1    6/2005    Freehauf

FOREIGN PATENT DOCUMENTS

EP      0 717 993 B1    3/2000
GB      2 252 730 B    12/1994
WO      WO 00/48636    8/2000

OTHER PUBLICATIONS

PCT International Search Report dated Dec. 15, 2004 for International Application No. PCT/US04/25005.

Virbac Corporation's Amended Complaint (93 pp.).

Parikh, Handbook of Pharmaceutical Granulation Technology; Drugs and the Pharmaceutical Sciences, 81; New York Marcel Dekker, Inc., 1997, pp. 51 and 52.

* cited by examiner

ANTHELMINTIC FORMULATIONS

CROSS REFERENCE TO RELATED APPLICATIONS

This application is a continuation-in-part of U.S. Ser. No. 10/637,807, filed Aug. 8, 2003. Priority is claimed to the application listed above, which is incorporated herein by reference.

BACKGROUND OF INVENTION

The invention relates generally to anthelmintic formulations which can have significant parasiticidal activity as anthelmintics, ectoparasiticides, insecticides and acaricides in animal health and more particularly to solid anthelmintic formulations containing ivermectin.

Active ingredients of anthelmintics and their methods of formation in accordance with preferred embodiments of the invention are discussed in e.g. U.S. Pat. Nos. 3,502,661, 3,954,791, 3,993,682, 4,001,411 and 4,199,569, the contents of which are incorporated herein by reference.

It is often beneficial, under certain circumstances, to include multiple drugs in the same formulation in order to target a wider variety of parasites. One particularly desirable anthelmintic composition is ivermectin. Ivermectin is hygroscopic and therefore tends to be undesirably unstable. It has also been seen that ivermectin is unstable in both acidic and basic solutions and is susceptible to photodegradation and oxidative degradation. Accordingly, it is very difficult to prepare a solid composition, such as a tablet, containing ivermectin without having to resort to using a large amount of filler material to make up the bulk of the tablet in order to maintain the integrity of the compound and even then, degradation problems can exist. This problem is compounded when additional drugs are intended to be included in the same formulation, as ivermectin can degrade or be degraded by other drugs.

Accordingly, it is desirable to provide a multidrug anthelmintic formulation in solid form that can be formed into a solid or tablet of optimal size, palatable to animals and which can be easily administered to the affected animal.

SUMMARY OF THE INVENTION

Generally speaking, in accordance with the invention, a pharmaceutical formulation is provided for use in the treatment of helminthiasis of mammals, and particularly tapeworm, hookworm, roundworm, whipworm and heartworm of domestic animals and farm animals. Accordingly, the present invention provides a method of treating helminthiasis in mammals, which method comprises administering to the mammal in need thereof, an anthelmintically effective amount of a pharmaceutical formulation of the invention. The present invention also provides a composition and a method for preparing a pharmaceutical formulation containing ivermectin and a method and composition that can contain ivermectin plus other active compositions such as hexahydropyrazinoisoquinolines, anthelmintic pyrimidines such as tetrahydropyrimidines and benzimidazoles or probenzimidazoles. An example of a hexahydropyrazinoisoquinoline is praziquantel and an example of a tetrahydropyrimidine is a pyrantel, such as pyrantel pamoate. An example of a benzimidazole is fenbendazole. An example of a probenzimidazole is febantel. Preferred formulations in accordance with the invention can remain stable for over one month, and typically, much longer.

One preferred method involves isolating the ivermectin through granulation, in particular, spray granulation. The other drugs can also be granulated or spray granulated. The granules can be left in a powder form, tabletted or packed into a capsule (i.e., encapsulated). One method of preparation of the formulation comprises the following steps:

(a) preparing a first and second; a first, second and third or a first, second, third and fourth (or more) combination including the first and second; the first, second and third or the first, second, third and fourth active ingredient, respectively;

(b) combining the combinations from (a) with dispersing agents to form two, three or four separate aqueous solutions;

(c) granulating one or all of the solutions, especially by spray granulation, from (b) by combining with a dry combination;

(d) drying the resulting granules, if needed;

(e) blending the granules from (d), which contain the first, second, third (and fourth) active ingredients and an excipient combination; and (f) forming the blended granules into tablets or capsules or leaving in powder form.

DETAILED DESCRIPTION OF THE PREFERRED EMBODIMENTS

The present invention relates to anthelmintic active compound combinations including avermectins or macrolide endectocides, hexahydropyrazinoisoquinolines, anthelmintic pyrimidines such as tetrahydropyrimidines and benzimidazoles or probenzimidazoles. Acceptable tetrahydropyrimidines include, for example, pyrantel, morantel and oxantel. An acceptable pyrantel that may be used is pyrantel pamoate. Acceptable hexahydropyrazinoisoquinolines include, for example, praziquantel. Acceptable macrolide endectocides include, for example, avermectins. Acceptable avermectins include, for example, ivermectin, doramectin, selamectin and abamectin. Acceptable benzimidazoles include, for example, mebendazole, oxibendazole, fenbendazole, oxfendazole, triclabendazole, flubendazole, ricobendazole, thiabendazole, and albendazole. Acceptable probenzimidazoles include, for example, febantel.

A formulation of active ingredients comprising ivermectin, praziquantel, pyrantel (pamoate) and fenbendazole or febantel is particularly preferred. The active ingredients target different pathogenic organisms that can adversely affect the health of a mammal. For example, ivermectin kills a variety of internal and external parasites; a number of worms including stomach worms, intestinal worms, lungworms, barber's worms, lice and mites. This particular combination is particularly effective in fighting a wide variety of organisms. However, administering four physically separate pharmaceutical compositions to an animal is undesirable and it has been determined that it would be beneficial to combine the ingredients into one formulation, in particular one tablet (or capsule) containing a pharmaceutically effective amount of the active ingredients, thereby decreasing the number of administrations of formulations to the animal. Thus, when the active ingredients are combined into a single formulation, the formulation provides protection against a broader spectrum of parasites than a formulation containing any parasitical agent alone. As used herein, the identification of an active ingredient, e.g. a benzimidazole or ivermectin, is intended to cover pharmaceutically active forms thereof such as salts, hydrochlorides, chelates, and so forth.

The formulation may also be useful in overcoming problems seen with single drug resistance. The inclusion of greater than one anthelmintic in the formulations discussed herein may have an increased likelihood of eliminating a particular helminth that is resistant to other included anthelmintic compounds. Even if the helminth is resistant to one, two or three of the ingredients, it is likely that at least one of the other ingredients will be effective at eliminating the helminth in question.

The disease or group of diseases described generally as helminthiasis is due to infestation of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. Repeat treatments are given as required to combat re-infestations and are dependent upon the species of parasite. The techniques for administering these materials to animals are known to those skilled in the field of veterinary medicine.

The preparations are suitable for combating pathogenic endoparasites which occur in animal husbandry and animal breeding in productive, breeding, zoo, laboratory, experimental animals and pets, and have a favorable toxicity to warm-blooded animals. In this connection, they are active against all or individual stages of development of the pests and against resistant and normally sensitive species. By combating pathogenic endoparasites, it is intended that disease, cases of death and reduction in production (for example in the production of meat, milk, wool, hides, eggs, etc.) are reduced so that more economic and simpler animal husbandry is possible by means of the use of the pharmaceutical formulation.

Productive and breeding animals include mammals, such as, for example, cattle, horses, sheep, pigs, goats, camels, water buffalo, donkeys, rabbits, fallow deer and reindeer, pelt animals, such as, for example, mink, chinchilla and raccoons, birds, such as, for example, chickens, geese, turkeys and ducks, fresh and salt-water fish, such as, for example, trout, carp and eels, and reptiles.

Laboratory and experimental animals include mice, rats, guinea pigs, hamsters, dogs and cats.

Pets include dogs and cats.

The formulation according to the invention is particularly preferably administered to dogs and cats, but is suitable for other mammals.

Administration can take place both prophylactically and therapeutically.

The formulations can be administered directly or in the form of suitable preparations, enterally, parenterally or dermally.

Enteral administration of the formulations takes place, for example, orally in the form of powder, tablets, capsules, pastes, potions, granules, orally administered solutions, suspensions and emulsions, boli, medicated feed or drinking water.

Suitable preparations are:
oral solutions and concentrates for oral administration after dilution;
emulsions and suspension for oral administration; and semisolid preparations;
formulations in which the active compound is processed in an ointment base or in an oil-in-water or water-in-oil emulsion base;
solid preparations, such as powders, premixes or concentrates, granules, pellets, tablets, caplets, boli and capsules, with tablets the preferred form;
oral solutions are prepared by dissolving the active compound in a suitable solvent and, if appropriate, adding additives such as solubilizers, acids, bases, buffer salts, antioxidants and preservatives. The solutions are filtered and packed under sterile conditions.

Solvents may include: physiologically acceptable solvents, such as water, alcohols, such as ethanol, butanol, benzyl alcohol, glycerol, propylene glycol and polyethylene glycol, N-methylpyrrolidone, and mixtures of the same.

The active compounds can, if appropriate, also be dissolved in physiologically acceptable vegetable or synthetic oils.

Solubilizers may include: solvents which promote dissolution of the active compound in the main solvent or substances which prevent precipitation of the active compound. Examples are polyvinyl pyrrolidone, polyoxyethylated castor oil and polyoxyethylated sorbitan esters.

One particularly preferred formulation of the invention, comprising four active ingredients, is preferably administered in the form of capsules, more preferably tablets. A preferred formulation of the present invention contains 0.005-25% ivermectin, preferably 0.01-15%, and most preferably 0.012-5%, with 0.013 or 0.016% as a preferred example. A preferred formulation of the present invention can contain 2.0-58% of a secondary anthelmintic drug, such as an isoquinoline, preferably praziquantel, preferably 6-41%, and most preferably 8.2-23%, with 8.7% or 10.56% as a preferred example. A preferred formulation of the present invention can contain 1.5-76% of an anthelmintic pyrimidine, preferably pyrantel, such as pyrantel pamoate, preferably 11.2-52%, and most preferably 21.2-33%, with 25.04% or 30.40% as a preferred example. A preferred formulation of the present invention can contain 25.3-62.5% of a benzimidazole, preferably fenbendazole, preferably 30.0-45.2%, and most preferably 35.3% as a preferred example. Instead of a benzimidazole, a preferred formulation of the present invention can contain 15.2-37.6% of a probenzimidazole, preferably febantel, preferably 19.4-31.6%, and most preferably 21.4%. All percentages herein, unless otherwise evident, are on a weight basis.

A preferred dosage of avermectin, e.g., ivermectin, is about 5-7 µg/Kg body weight of the animal administered monthly, preferably 5.5-6.5 µg/Kg body weight, with 6 µg/Kg body weight as a preferred example. A preferred dosage of anthelmintic pyrimidines, e.g., pyrantel pamoate, is about 4.25-5.75 mg/Kg body weight administered monthly, preferably 4.75-5.25 mg/Kg, with 5 mg as a preferred example. A preferred dosage of hexahydropyrazinoisoquinaline, e.g., praziquantel, is about 4.25-5.75 mg/Kg body weight administered monthly, preferably 4.75-5.25 mg/Kg, with 5 mg as a preferred example. A preferred dosage of benzimidazole, e.g., fenbendazole, is about 37-63 mg/Kg body weight administered monthly, preferably 42-58 mg/Kg, with 50 mg as a preferred example. A preferred dosage of febantel, is about 18-32 mg/Kg body weight administered monthly, preferably 21-29 mg/Kg, with 25 mg as a preferred example.

To prepare solid preparations, the active compound should be mixed with suitable excipients, if appropriate, with addition of auxiliaries, and converted to the form desired.

One preferred method of preparation of the formulation comprises the following steps:

(a) preparing a first and second; a first, second and third or a first, second, third and fourth (or more) combination including the first and second; the first, second and third or the first, second, third and fourth active ingredient, respectively;

(b) combining the combinations from (a) with dispersing agents to form two, three or four separate aqueous solutions;

(c) granulating one or all of the solutions, especially by spray granulation, from (b) by combining with a dry combination;

(d) drying the resulting granules, if needed;

(e) blending the granules from (d), which contain the first, second, third (and fourth) active ingredients and an excipient combination; and (f) forming the blended granules into tablets or capsules or leaving in powder form.

Spray granulation involves the spraying of liquid (i.e., solution, suspension melt and so forth) onto a powder or granules while simultaneously building particle size and removing the volatile liquid by drying. By mixing an active ingredient with a carrier in the liquid phase, the active can become "encapsulated" or substantially covered in a matrix of carrier after the spray granulation process. Granulation is generally performed by spraying liquid into the fluidized powder. The granules can subsequently be dried with heated air.

Suitable excipients may include physiologically acceptable inert solids such as, for example, sodium chloride, calcium carbonate, hydrogen carbonates, aluminum oxides, silicas, clays, precipitated or colloidal silicon dioxide and phosphates. Other suitable excipients may include, for example, sugar, cellulose, Croscarmellose Sodium (i.e., carboxymethyl cellulose), Aerosil, nutrients and feedstuffs, such as milk powder and pork liver powder, animal meals, ground and crushed cereal meals, Avicel PH102 and starches.

Auxiliaries can include preservatives, antioxidants and colorants. Additional suitable auxiliaries can include lubricants, such as, for example, magnesium stearate, stearic acid, talcum and bentonites, disintegration-promoting substances, such as starch or transversely crosslinked polyvinyl pyrrolidone, binders, such as, for example, starch, gelatin or linear polyvinyl pyrrolidone, and dry binders, such as microcrystalline cellulose.

The formulation can also be in the form of a chewable, such as a beef-chewable containing ground or minced beef or other meat, in addition to other excipients listed above.

The materials in the final formulation, such as the excipients, auxiliaries, synergists and other materials, which aid in delivery, shelf-life, desired physical structure and so forth will be referred to herein generally as carrier material. As stated herein, carrier material could be pharmaceutically active under certain circumstances.

The following examples are given for purposes of illustration only and are not intended to be construed in a limiting manner.

EXAMPLE 1

Preparation of Tablets or Caplets Containing Ivermectin, Praziquantel, Pyrantel and Fenbendazole Four separate mixtures were prepared as follows:
Mixture A:

TABLE 1

| Ingredient | Amount (g) | % w/w |
| --- | --- | --- |
| Ivermectin | 8.3 | 0.013 |
| Microcrystalline Cellulose USP (Avicel PH102) | 2640.0 | 3.38 |
| Povidone K30 | 2143.0 | 2.75 |
| Croscarmellose Sodium | 855.0 | 1.10 |
| Polyethylene Glycol 8005 | 500.0 | 0.64 |
| Citric Acid Anhydrous | 10.4 | 0.013 |
| Sodium Citrate Dihydrate | 3.5 | 0.0045 |
| Purified Water | 1961.5 | |

The ingredients were dispensed in the amounts specified in Table 1.

The following materials (in the order listed below) were passed through a Russel Sieve fitted with 20# sieve and collected in a stainless steel drum:

(a) Avicel PH102

(b) Croscarmellose Sodium (c) Povidone

The delumped material resulting from the step above was added to the drum tumbler and blended for 20 minutes. Purified water was added to a stock pot with citric acid and sodium citrate dihydrate. The contents were mixed for 5 minutes with a stirring rod.

Polyethylene glycol flakes were added to a separate stock pot and heated with a water bath to a temperature of 50-65° C. to melt the flakes. The solution was maintained at this temperature. Ivermectin was added to the melted polyethylene glycol with gentle stirring until the compound was dissolved. The solution was maintained at 50-65° C.

161.5 g of the citrate buffer detailed above was added to the melted polyethylene glycol/ivermectin solution and stirred with gentle agitation for at least 5 minutes until the solution was clear. The stirring was then ceased to allow any air bubbles to escape and the solution was maintained at 50-65° C.

The remaining citrate buffer solution was placed on a hot plate and heated to a temperature of 55±50° C.

The blended Avicel, Croscarmellose Sodium and Povidone was transferred to a spray granulator. The solutions were spray granulated as follows:

(a) The spray granulator was programmed with the following parameters:

(1) inlet air temperature: 50±10° C.

(2) outlet air temperature: 45±10° C.

(3) bed temperature: 43±10° C.

(4) atomization pressure: 3-5 bar (5) spray rate: 100 g±20 g per minute (6) pan speed: 2-10 rpm (b) The ivermectin/polyethylene glycol/citrate buffer solutions was sprayed at a rate of 100±20 g/minute until all of the solution was sprayed.

(c) The reserve citrate buffer at 55±5° C. was added to the container which held the previous solution for rinsing purposes. The rinse citrate buffer was sprayed at a rate of 100±20 g/minute.

(d) Granulation was continued by spraying 300 g of purified water at room temperature. Additional purified water was sprayed until the desired consistency was achieved.

The granules were then emptied into the drying bowl and dried using a fluid bed drier. After drying, the bowl was removed and the granules were mixed with a scoop. The dried granules obtained were transferred in double polythene lined suitable container.

Mixture B:

TABLE 2

| Ingredient | Amount (g) | % w/w |
|---|---|---|
| Pyrantel Pamoate | 19,536.0 | 25.04 |
| Microcrystalline Cellulose USP (Avicel PH102) | 2,285.0 | 2.93 |
| Croscarmellose Sodium | 810.0 | 1.04 |
| Povidone K30 | 630.0 | 0.81 |
| Fenbendazole | 29,763 | 35.26 |

The ingredients were dispensed in the amounts specified in Table 2.

The following materials (in the order listed below) were passed through a Russel Sieve fitted with 20# sieve and collected in a suitable container:

(a) Pyrantel Pamoate
(b) Fenbendazole
(c) Povidone
(d) Croscarmellose Sodium
(e) Avicel PH102

The sieved material was added to a Diosna mixer and blended for 10 minutes using the impeller on low speed with the chopper off. The mixture was granulated with 9,000 g of purified water with the impeller and the chopper set on low speed. Additional purified water was added to achieve the good granular mass.

The granulated mixture was dried using a fluid bed drier and transferred to a double polythene lined suitable container.

Mixture C:

TABLE 3

| Ingredient | Amount (g) | % w/w |
|---|---|---|
| Praziquantel USP | 6,786.0 | 8.70 |
| Povidone K30 | 715.0 | 0.92 |
| Croscarmellose Sodium | 835.0 | 1.07 |
| Polymethacrylate USP (Eudragit E-100) | 2,530.0 | 3.24 |
| Citric Acid Anhydrous | 789.4 | 1.01 |
| Microcrystalline Cellulose USP (Avicel PH102) | 1,785.0 | 2.93 |
| Purified Water | See Below | |

The ingredients were dispensed in the amounts specified in Table 3.

The following materials (in the order listed below) were passed through a Russel Sieve fitted with 20# sieve and collected in a stainless steel drum:

(a) Praziquantel USP
(b) Povidone
(c) Croscarmellose Sodium
(d) Avicel PH102

The delumped material was mixed in a drum tumbler for 20 minutes. The mixture was added to a Diosna mixer and 10 L of purified water was gradually added with the impeller on low speed with the chopper activated for 5 minutes. The choppers were set on fast speed and run for 3 minutes. The granules were dried in a fluid bed drier and transferred to a double polythene lined suitable container.

13,658 g of purified water was added to a stock pot and mixed with medium agitation. Citric acid and Eudragit E-100 was added to the stock pot. The mixture was stirred with medium agitation until the components had completely dissolved. The resulting Eudragit solution was allowed to settle until the air bubbles had escaped.

The praziquantel/fenbendazole granulated mixture was added to the spray granulator and coated with the Eudragit E-100 solution. The resulting material was transferred to a double polythene lined suitable container.

Excipient Mixture:

TABLE 4

| Ingredient | Amount (g) | % w/w |
|---|---|---|
| SD Pork Liver Powder | 4,048.0 | 5.19 |
| Avicel PH102 | 1,663.0 | 2.13 |
| Croscarmellose Sodium | 778.0 | 1.01 |
| Aerosil | 150.0 | 0.19 |
| Magnesium Stearate | 500.0 | 0.64 |

The ingredients were dispensed in the amounts specified in Table 4.

The first four excipients were sifted through a 500# sieve and collected in a suitable container. Then the Magnesium Stearate was sifted through a 500# mesh sieve. The four mixtures containing the active ingredients of the formulation (i.e., Mixtures A, B and C) and the excipient mixture were blended in a drum tumbler for 25 minutes. The sifted Magnesium Stearate was added and blended for an additional 5 minutes.

The formulation was then either compressed into tablets or caplets of 1800 mg or 3600 mg or the granules were packaged into sachets.

EXAMPLE 2

Preparation of Tablets or Caplets Containing Ivermectin, Praziquantel, Pyrantel and Febantel Four separate mixtures were prepared as follows:

Mixture D:

TABLE 5

| Ingredient | Amount (g) | % w/w |
|---|---|---|
| Ivermectin | 8.3 | 0.016 |
| Microcrystalline Cellulose USP (Avicel PH102) | 2640.0 | 4.11 |
| Povidone K30 | 2143.0 | 3.34 |
| Croscarmellose Sodium | 855.0 | 1.33 |
| Polyethylene Glycol 8005 | 500.0 | 0.78 |
| Citric Acid Anhydrous | 10.4 | 0.015 |
| Sodium Citrate Dihydrate | 3.5 | 0.005 |
| Purified Water | 1961.5 | |

The ingredients were dispensed in the amounts specified in Table 5.

The following materials (in the order listed below) were passed through a Russel Sieve fitted with 20# sieve and collected in a stainless steel drum:

(a) Avicel PH102
(b) Croscarmellose Sodium
(c) Povidone

The delumped material resulting from the step above was added to the drum tumbler and blended for 20 minutes. Purified water was added to a stock pot with citric acid and sodium citrate dihydrate. The contents were mixed for 5 minutes with a stirring rod.

Polyethylene glycol flakes were added to a separate stock pot and heated with a water bath to a temperature of 50-65° C. to melt the flakes. The solution was maintained at this temperature. Ivermectin was added to the melted polyethylene glycol with gentle stirring until the compound was dissolved. The solution was maintained at 50-65° C.

161.5 g of the citrate buffer detailed above was added to the melted polyethylene glycol/ivermectin solution and stirred with gentle agitation for at least 5 minutes until the solution was clear. The stirring was then ceased to allow any air bubbles to escape and the solution was maintained at 50-65° C.

The remaining citrate buffer solution was placed on a hot plate and heated to a temperature of 55±5° C.

The blended Avicel, Croscarmellose Sodium and Povidone was transferred to a spray granulator. The solutions were spray granulated as follows:

(a) The spray granulator was programmed with the following parameters:
  (1) inlet air temperature: 50±10° C.
  (2) outlet air temperature: 45±10° C.
  (3) bed temperature: 43±10° C.
  (4) atomization pressure: 3-5 bar
  (5) spray rate: 100 g±20 g per minute
  (6) pan speed: 2-10 rpm
(b) The ivermectin/polyethylene glycol/citrate buffer solutions was sprayed at a rate of 100±20 g/minute until all of the solution was sprayed.
(c) The reserve citrate buffer at 55±5° C. was added to the container which held the previous solution for rinsing purposes. The rinse citrate buffer was sprayed at a rate of 100±20 g/minute.
(d) Granulation was continued by spraying 300 g of purified water at room temperature. Additional purified water was sprayed until the desired consistency was achieved.

The granules were then emptied into the drying bowl and dried using a fluid bed drier. After drying, the bowl was removed and the granules were mixed with a scoop. The dried granules obtained were transferred in double polythene lined suitable container.

Mixture E:

TABLE 6

| Ingredient | Amount (g) | % w/w |
|---|---|---|
| Pyrantel Pamoate | 19,536.0 | 30.40 |
| Microcrystalline Cellulose USP (Avicel PH102) | 2,285.0 | 3.56 |
| Croscarmellose Sodium | 810.0 | 1.26 |
| Povidone K30 | 630.0 | 0.98 |
| Febantel | 14,881 | 21.40 |

The ingredients were dispensed in the amounts specified in Table 6.

The following materials (in the order listed below) were passed through a Russel Sieve fitted with 20# sieve and collected in a suitable container:
(a) Pyrantel Pamoate
(b) Febantel
(c) Povidone
(d) Croscarmellose Sodium
(e) Avicel PH102

The sieved material was added to a Diosna mixer and blended for 10 minutes using the impeller on low speed with the chopper off. The mixture was granulated with 9,000 g of purified water with the impeller and the chopper set on low speed. Additional purified water was added to achieve the good granular mass.

The granulated mixture was dried using a fluid bed drier and transferred to a double polythene lined suitable container.

Mixture F:

TABLE 7

| Ingredient | Amount (g) | % w/w |
|---|---|---|
| Praziquantel USP | 6,786.0 | 10.56 |
| Povidone K30 | 715.0 | 1.11 |
| Croscarmellose Sodium | 835.0 | 1.30 |
| Polymethacrylate USP (Eudragit E-100) | 2,530.0 | 3.94 |
| Citric Acid Anhydrous | 789.4 | 1.23 |
| Microcrystalline Cellulose USP (Avicel PH102) | 1,785.0 | 3.56 |
| Purified Water | See Below | |

The ingredients were dispensed in the amounts specified in Table 7.

The following materials (in the order listed below) were passed through a Russel Sieve fitted with 20# sieve and collected in a stainless steel drum:
(a) Praziquantel USP
(b) Povidone
(c) Croscarmellose Sodium
(d) Avicel PH102

The delumped material was mixed in a drum tumbler for 20 minutes. The mixture was added to a Diosna mixer and 10 L of purified water was gradually added with the impeller on low speed with the chopper activated for 5 minutes. The choppers were set on fast speed and run for 3 minutes. The granules were dried in a fluid bed drier and transferred to a double polythene lined suitable container.

13,658 g of purified water was added to a stock pot and mixed with medium agitation. Citric acid and Eudragit E-100 was added to the stock pot. The mixture was stirred with medium agitation until the components had completely dissolved. The resulting Eudragit solution was allowed to settle until the air bubbles had escaped.

The praziquantel/febantel granulated mixture was added to the spray granulator and coated with the Eudragit E-100 solution. The resulting material was transferred to a double polythene lined suitable container.

Excipient Mixture:

TABLE 8

| Ingredient | Amount (g) | % w/w |
|---|---|---|
| SD Pork Liver Powder | 4,048.0 | 6.30 |
| Avicel PH102 | 1,663.0 | 2.59 |
| Croscarmellose Sodium | 778.0 | 1.23 |
| Aerosil | 150.0 | 0.23 |
| Magnesium Stearate | 500.0 | 0.78 |

The ingredients were dispensed in the amounts specified in Table 8.

The first four excipients were sifted through a 500# sieve and collected in a suitable container. Then the Magnesium Stearate was sifted through a 500# mesh sieve. The four mixtures containing the active ingredients of the formulation (i.e., Mixtures D, E and F) and the excipient mixture were blended in a drum tumbler for 25 minutes. The sifted Magnesium Stearate was added and blended for an additional 5 minutes.

The formulation was then either compressed into tablets or caplets of 1800 mg or 3600 mg or the granules were packaged into sachets.

EXAMPLE 3

Non-Aqueous Preparation of Tablets or Caplets Containing Ivermectin, Praziquantel, Pyrantel and Fenbendazole Four separate mixtures were prepared as follows:
Mixture G:

TABLE 9

| Ingredient | Amount (g) | % w/w |
|---|---|---|
| Ivermectin | 67 | 0.013 |
| Microcrystalline Cellulose USP (Avicel PH102) | 17076 | 3.31 |
| Povidone K30 | 13861 | 2.69 |
| Croscarmellose Sodium | 5530 | 1.07 |
| Ethanol | 12165 | N/A |

The ingredients were dispensed in the amounts specified in Table 9.

The following materials (in the order listed below) were passed through a Russel Sieve fitted with 20# sieve and collected in a stainless steel drum:
(a) Avicel PH102
(b) Croscarmellose Sodium
(c) Povidone The delumped material resulting from the step above was added to the drum tumbler and blended for 20 minutes. Ivermectin was added to the ethanol with gentle stirring at room temperature until the compound was dissolved.

The blended Avicel, Croscarmellose Sodium and Povidone was transferred to a spray granulator. The solutions were spray granulated as follows:
(a) The spray granulator was programmed with the following parameters:
  (1) inlet air temperature: 50±10° C.
  (2) outlet air temperature: 45±10° C.
  (3) bed temperature: 43±10° C.
  (4) atomization pressure: 3-5 bar
  (5) spray rate: 100 g±20 g per minute
  (6) pan speed: 2-10 rpm
(b) The ivermectin solution was sprayed at a rate of 100±20 g/minute until all of the solution was sprayed.
(c) Granulation was continued by spraying 300 g of ethanol at room temperature. Additional ethanol was sprayed until the desired consistency was achieved.

The granules were then emptied into the drying bowl and dried using a fluid bed drier. After drying, the bowl was removed and the granules were mixed with a scoop. The dried granules obtained were transferred in double polythene lined suitable container.
Mixture H:

TABLE 10

| Ingredient | Amount (g) | % w/w |
|---|---|---|
| Pyrantel Pamoate | 126359 | 24.49 |
| Microcrystalline Cellulose USP (Avicel PH102) | 14779 | 2.86 |

TABLE 10-continued

| Ingredient | Amount (g) | % w/w |
|---|---|---|
| Croscarmellose Sodium | 5239 | 1.01 |
| Povidone K30 | 4075 | 0.79 |
| Fenbendazole | 192507 | 37.73 |
| Isopropyl alcohol | 50000 | N/A |

The ingredients were dispensed in the amounts specified in Table 10.

The following materials (in the order listed below) were passed through a Russel Sieve fitted with 20# sieve and collected in a suitable container:
(a) Pyrantel Pamoate
(b) Fenbendazole
(c) Povidone
(d) Croscarmellose Sodium
(e) Avicel PH102

The sieved material was added to a Diosna mixer and blended for 10 minutes using the impeller on low speed with the chopper off. The mixture was granulated with 50,000 g of isopropyl alcohol with the impeller and the chopper set on low speed. Additional isopropyl alcohol was added to achieve the good granular mass.

The granulated mixture was dried using a fluid bed drier and transferred to a double polythene lined suitable container.
Mixture I:

TABLE 11

| Ingredient | Amount (g) | % w/w |
|---|---|---|
| Praziquantel USP | 6,786.0 | 8.70 |
| Povidone K30 | 715.0 | 0.92 |
| Croscarmellose Sodium | 835.0 | 1.07 |
| Microcrystalline Cellulose USP (Avicel PH102) | 1,785.0 | 2.93 |
| Isopropyl alcohol | See Below | |

The ingredients were dispensed in the amounts specified in Table 11.

The following materials (in the order listed below) were passed through a Russel Sieve fitted with 20# sieve and collected in a stainless steel drum:
(a) Praziquantel USP
(b) Povidone
(c) Croscarmellose Sodium
(d) Avicel PH102

The delumped material was mixed in a drum tumbler for 20 minutes. The mixture was added to a Diosna mixer and 28,684 g of isopropyl alcohol was gradually added with the impeller on low speed with the chopper activated for 5 minutes. The choppers were set on fast speed and run for 3 minutes. The granules were dried in a fluid bed drier and transferred to a double polythene lined suitable container.
Excipient Mixture:

TABLE 12

| Ingredient | Amount (g) | % w/w |
|---|---|---|
| SD Pork Liver Powder | 26182 | 5.07 |
| Avicel PH102 | 10756 | 2.08 |
| Croscarmellose Sodium | 8332 | 1.62 |
| Aerosil | 970 | 0.19 |
| Magnesium Stearate | 3234 | 0.63 |

The ingredients were dispensed in the amounts specified in Table 12.

The first four excipients were sifted through a 500# sieve and collected in a suitable container. Then the Magnesium Stearate was sifted through a 500# mesh sieve. The four mixtures containing the active ingredients of the formulation (i.e., Mixtures G, H and I) and the excipient mixture were blended in a drum tumbler for 25 minutes. The sifted Magnesium Stearate was added and blended for an additional 5 minutes.

The formulation was then either compressed into tablets or caplets of 1800 mg or 3600 mg or the granules were packaged into sachets.

EXAMPLE 4

Non-Aqueous Preparation of Tablets or Caplets Containing Ivermectin, Praziquantel, Pyrantel and Febantel Four separate mixtures were prepared as follows:
Mixture J:

TABLE 13

| Ingredient | Amount (g) | % w/w |
| --- | --- | --- |
| Ivermectin | 67 | 0.016 |
| Microcrystalline Cellulose USP (Avicel PH102) | 17076 | 4.10 |
| Povidone K30 | 13861 | 3.30 |
| Sodium Citrate Dihydrate | 5530 | 1.32 |
| Ethanol | 12165 | N/A |

The ingredients were dispensed in the amounts specified in Table 13.

The following materials (in the order listed below) were passed through a Russel Sieve fitted with 20# sieve and collected in a stainless steel drum:
(a) Avicel PH102
(b) Croscarmellose Sodium
(c) Povidone The delumped material resulting from the step above was added to the drum tumbler and blended for 20 minutes.

Ivermectin was added to the ethanol with gentle stirring at room temperature until the compound was dissolved.

The blended Avicel, Croscarmellose Sodium and Povidone was transferred to a spray granulator. The solutions were spray granulated as follows:
(a) The spray granulator was programmed with the following parameters:
  (1) inlet air temperature: 50±10° C.
  (2) outlet air temperature: 45±10° C.
  (3) bed temperature: 43±10° C.
  (4) atomization pressure: 3-5 bar
  (5) spray rate: 100 g±20 g per minute
  (6) pan speed: 2-10 rpm
(b) The ivermectin solutions was sprayed at a rate of 100±20 g/minute until all of the solution was sprayed.
(c) Granulation was continued by spraying 300 g of ethanol at room temperature. Additional ethanol was sprayed until the desired consistency was achieved.

The granules were then emptied into the drying bowl and dried using a fluid bed drier. After drying, the bowl was removed and the granules were mixed with a scoop. The dried granules obtained were transferred in double polythene lined suitable container.

Mixture K:

TABLE 14

| Ingredient | Amount (g) | % w/w |
| --- | --- | --- |
| Pyrantel Pamoate | 126359 | 30.11 |
| Microcrystalline Cellulose USP (Avicel PH102) | 14779 | 3.52 |
| Croscarmellose Sodium | 5239 | 1.25 |
| Povidone K30 | 4075 | 0.97 |
| Febantel | 96254 | 22.94 |

The ingredients were dispensed in the amounts specified in Table 14.

The following materials (in the order listed below) were passed through a Russel Sieve fitted with 20# sieve and collected in a suitable container:
(a) Pyrantel Pamoate
(b) Febantel
(c) Povidone
(d) Croscarmellose Sodium
(e) Avicel PH102

The sieved material was added to a Diosna mixer and blended for 10 minutes using the impeller on low speed with the chopper off. The mixture was granulated with 9,000 g of isopropyl alcohol with the impeller and the chopper set on low speed. Additional isopropyl alcohol was added to achieve the good granular mass.

The granulated mixture was dried using a fluid bed drier and transferred to a double polythene lined suitable container.

Mixture L:

TABLE 15

| Ingredient | Amount (g) | % w/w |
| --- | --- | --- |
| Praziquantel USP | 43892 | 10.46 |
| Povidone K30 | 4625 | 1.10 |
| Croscarmellose Sodium | 5400 | 1.29 |
| Microcrystalline Cellulose USP (Avicel PH102) | 33019 | 7.87 |
| Isopropyl alcohol | 28684 | N/A |

The ingredients were dispensed in the amounts specified in Table 15.

The following materials (in the order listed below) were passed through a Russel Sieve fitted with 20# sieve and collected in a stainless steel drum:
(a) Praziquantel USP
(b) Povidone
(c) Croscarmellose Sodium
(d) Avicel PH102

The delumped material was mixed in a drum tumbler for 20 minutes. The mixture was added to a Diosna mixer and 28,684 g of isopropyl alcohol was gradually added with the impeller on low speed with the chopper activated for 5 minutes. The choppers were set on fast speed and run for 3 minutes. The granules were dried in a fluid bed drier and transferred to a double polythene lined suitable container.

Excipient Mixture:

TABLE 16

| Ingredient | Amount (g) | % w/w |
| --- | --- | --- |
| SD Pork Liver Powder | 26182 | 6.24 |
| Avicel PH102 | 10756 | 2.56 |
| Croscarmellose Sodium | 8332 | 1.98 |
| Aerosil | 970 | 0.23 |
| Magnesium Stearate | 3234 | 0.77 |

The ingredients were dispensed in the amounts specified in Table 16.

The first four excipients were sifted through a 500# sieve and collected in a suitable container. Then the Magnesium Stearate was sifted through a 500# mesh sieve. The four mixtures containing the active ingredients of the formulation (i.e., Mixtures J, K and L) and the excipient mixture were blended in a drum tumbler for 25 minutes. The sifted Magnesium Stearate was added and blended for an additional 5 minutes. The formulation was then either compressed into tablets or caplets of 1800 mg or 3600 mg or the granules were packaged into sachets.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween. Particularly it is to be understood that in said claims, ingredients or compounds recited in the singular are intended to include compatible mixtures of such ingredients wherever the sense permits.

What is claimed is:

1. A pharmaceutically acceptable solid anthelmintic formulation comprising a combination of
    a first active ingredient comprising particles of an avermectin spray granulated with polyethylene glycol around the particles;
    a second active ingredient comprising an anthelmintic pyrimidine;
    a third active ingredient comprising a hexahydropyrazinoisoquinoline; and
    a fourth active ingredient comprising a benzimidazole or probenzimidazole,
    wherein the polyethylene glycol coats the avermectin separating the avermectin from the second, third and fourth active ingredients.

2. The formulation of claim 1, wherein the first active ingredient comprises ivermectin.

3. The formulation of claim 1, comprising at least about 0.005% ivermectin.

4. The formulation of claim 1, comprising about 0.012-5% ivermectin.

5. The formulation of claim 1, comprising a tetrahydropyrimidine.

6. The formulation of claim 1, wherein the second active ingredient comprises a pyrantel.

7. The formulation of claim 6, wherein the pyrantel comprises pyrantel pamoate.

8. The formulation of claim 1, comprising at least about 1.5% pyrantel.

9. The formulation of claim 1, comprising about 11.2-33% pyrantel.

10. The formulation of claim 1, wherein the third active ingredient comprises praziquantel.

11. The formulation of claim 1, comprising at least about 2.0% praziquantel.

12. The formulation of claim 1, comprising about 8.2-23% praziquantel.

13. The formulation of claim 1, comprising at least about 25.3% fenbendazole.

14. The formulation of claim 1, comprising about 30.0-45.0% fenbendazole.

15. The formulation of claim 1, comprising at least about 15.2% febantel.

16. The formulation of claim 1, comprising about 19.4-31.6% febantel.

17. The formulation of claim 2, in a form that will remain stable and pharmaceutically active, in a solid form, for over one month.

18. The formulation of claim 17, wherein there is an effective amount of polyethylene glycol to prevent the ivermectin from degrading sufficiently to eliminate its pharmaceutical effectiveness.

19. A method for forming an anthelmintic formulation comprising the steps of:
    (A) preparing a combination of ivermectin and polyethylene glycol;
    (B) spray granulating the combination to form granules, with the polyethylene glycol covering the ivermectin; and
    (C) combining the granules with an additional active ingredient composition.

20. The method of claim 19, wherein the additional active ingredient composition comprises pyrantel pamoate, praziquantel, and fenbendazole or febantel.

21. The method of claim 19, wherein the formulation is pressed into a tablet or enclosed in a capsule and the ivermectin has been effectively isolated, so that the formulation will stay stable for over one month.

22. An anthelmintic formulation, which is formed by the method of claim 19.

23. A method of controlling helminth infestation in animals, comprising the step of administering a pharmaceutically effective amount of the formulation of claim 2 to an animal in need thereof.

24. The method of claim 23, wherein the animal is a dog or cat.

25. The method of claim 23, wherein the administration comprises administering 5-7 µg/Kg body weight of the dog or cat.

* * * * *

UNITED STATES PATENT AND TRADEMARK OFFICE
CERTIFICATE OF CORRECTION

PATENT NO. : 7,396,820 B2
APPLICATION NO. : 10/800407
DATED : July 8, 2008
INVENTOR(S) : Cottrell et al.

It is certified that error appears in the above-identified patent and that said Letters Patent is hereby corrected as shown below:

Title Page in the References Cited (56):

Please insert --6,383,471 B1 5/2002 Chen et al.--;

In the Detailed Description of the Preferred Embodiments:

Column 6, Line 48, please delete "55±50°" and insert --55±5°-- therefor.

Signed and Sealed this

Twenty-fifth Day of November, 2008

JON W. DUDAS
*Director of the United States Patent and Trademark Office*